US 9,451,874 B2

(12) United States Patent
Bromwich (10) Patent No.: US 9,451,874 B2
(45) Date of Patent: Sep. 27, 2016

(54) ADAPTER TO COUPLE A MOBILE PHONE TO AN ENDOSCOPE

(71) Applicant: Matthew Bromwich, Ottawa (CA)

(72) Inventor: Matthew Bromwich, Ottawa (CA)

(73) Assignee: Clearwater Clinical Limited, Calgary (CA)

( * ) Notice: Subject to any disclaimer, the term of this patent is extended or adjusted under 35 U.S.C. 154(b) by 163 days.

(21) Appl. No.: 14/080,341

(22) Filed: Nov. 14, 2013

(65) Prior Publication Data

US 2014/0142390 A1 May 22, 2014

Related U.S. Application Data

(60) Provisional application No. 61/727,465, filed on Nov. 16, 2012.

(51) Int. Cl.
*A61B 1/00* (2006.01)
*A61B 1/04* (2006.01)

(52) U.S. Cl.
CPC ....... *A61B 1/00131* (2013.01); *A61B 1/00126* (2013.01); *A61B 1/042* (2013.01); *A61B 2562/225* (2013.01)

(58) Field of Classification Search
USPC .......................... 600/102, 160; 396/419, 429
See application file for complete search history.

(56) References Cited

U.S. PATENT DOCUMENTS 8,376,301 B2 * 2/2013 Fan ...................... F16M 11/041
248/231.21
2006/0215013 A1 9/2006 Jongsma et al.

FOREIGN PATENT DOCUMENTS

WO WO2012/154578 11/2012
WO WO-2012/154587 A2 11/2012

OTHER PUBLICATIONS

Advertisement—Apple iPhone Mobile Phone Telescope (1st Gen.) [retrieved on Nov. 5, 2013 from the Internet:<URL: http://mobile.brando.com/prod_detail.php?prod_id=03112] (4 pages).
Advertisement—iPhone Microscope Camera Adapter—Skylight [retrieved on Nov. 5, 2013 from the Internet:<URL: http://www.skylightscope.com] (6 pages).
Advertisement—Magnifi—World's First iPhone Photoadapter Case [retrieved on Nov. 5, 2013 from the Internet:<URL: http://www/arcturuslabs.com] (12 pages).
Advertisement—xion medical—nomad C—Portable ENT Endoscopy and Documentation System (1 page).

(Continued)

*Primary Examiner* — Matthew J Kasztejna
(74) *Attorney, Agent, or Firm* — Harness, Dickey & Pierce, P.L.C.

(57) ABSTRACT

A scope adapter for coupling a phone to an endoscope includes a base having a phone receiving portion for receiving and releasably supporting a phone. A first base end and a second base end define extents of a base cavity. A shaft is connected at opposite ends to each of the first and second base ends and spans across the base cavity. A threaded shaft is rotationally supported at opposite ends to the first and second base ends and spans across the base cavity. An endoscope positioned within the cavity is movably disposed along the shaft in each of a first direction and an opposite second direction by axial rotation of the threaded shaft. The endoscope includes a lens aperture that is positioned with respect to the phone receiving portion by displacement of the endoscope in either the first or second directions.

6 Claims, 10 Drawing Sheets

(56) References Cited

OTHER PUBLICATIONS

RVA Smart Clamp Endoscope Adapter for Mobile Phones: found at: http://www.youtube.com/watch?v-opPBLZYkfCS: published on line Apr. 11, 2012.

Marlin's Accessories, "M-mount for Cell Phone and GPS", Youtube video found at: http://www.youtube.com/watch?v-TuAMGxcTtJ0, Nov. 13, 2010.
Cell Phone Based Platform for Biomedical Device Development and Education Applications: PloS One website: found at www.plosone.org; Published Mar. 2011; vol. 6, issue 3.

* cited by examiner

FIG 10

ADAPTER TO COUPLE A MOBILE PHONE TO AN ENDOSCOPE

CROSS-REFERENCE TO RELATED APPLICATIONS

This application claims the benefit of U.S. Provisional Application No. 61/727,465, filed on Nov. 16, 2012. The entire disclosure of the above application is incorporated herein by reference.

FIELD

The present disclosure relates to mobile telephone adapters used to mount viewing lens components to an endoscope.

BACKGROUND

This section provides background information related to the present disclosure which is not necessarily prior art.

Endoscopes are used by medical personnel such as fiberoptic flexible or rigid naso-pharyngoscopes to examine the throat, larynx or sinuses of a patient, as well as for examining gastrointestinal and pulmonary examinations. Presently, video capture devices are connected to the fiberoptic endoscope to display a video image at a distant display to assist in the examination. Adapters are known that permit the endoscope to be connected to a portable device such as a phone or "smart phone" where the phone includes its own internal camera and display system. Known adapters used for this purpose do not permit sufficient motion of the camera with respect to the endoscope viewing lens to allow flexibility of connection to multiple different phones, or to allow repeatable installation of many different phones to the same adapter to repeat an initially determined position of each phone without requiring significant realignment of the adapter.

SUMMARY

This section provides a general summary of the disclosure, and is not a comprehensive disclosure of its full scope or all of its features.

According to several aspects, a scope adapter for coupling a phone to an endoscope includes a base having a phone receiving portion for receiving and releasably supporting a phone. A first base end and a second base end define extents of a base cavity. A shaft is connected at opposite ends to each of the first and second base ends and spans across the base cavity. A telescopic lens component is positioned within the cavity and is movably disposed along the shaft in each of a first direction and an opposite second direction. The telescopic lens component includes a lens aperture that is positioned with respect to the phone receiving portion by displacement of the telescopic lens component in either the first or second directions.

According to further aspects, a scope adapter for coupling a phone to an endoscope includes a base having a phone receiving portion for receiving and releasably supporting a phone. A first base end and a second base end define extents of a base cavity. A threaded shaft is rotationally supported at opposite ends to each of the first and second base ends and spans across the base cavity. A telescopic lens component positioned within the cavity is movably disposed in each of a first direction and an opposite second direction by axial rotation of the threaded shaft. The telescopic lens component includes a lens aperture that is positioned with respect to the phone receiving portion by displacement of the telescopic lens component in either the first or second directions.

According to further aspects, a scope adapter for coupling a phone to an endoscope includes a base having a planar surface and a phone receiving portion, the planar surface extending into the phone receiving portion such that a phone received in the phone receiving portion is positioned on the planar surface. Opposed first and second clamps are oppositely positioned about the phone receiving portion having at least one of the clamps biased toward the other to releasably retain the phone. An L-shaped bar includes a bar first portion and a bar second portion oriented perpendicular to the bar first portion. The bar first portion is slidably and retractably received in one of the clamps having the bar second portion adjustably positioned to retain a position of the phone. A first base end and a second base end together define extents of a base cavity. A shaft is non-rotationally fixed at opposite ends to each of the first and second base ends and spans across the base cavity. A telescopic lens component is positioned within the cavity and is slidably disposed along the shaft, the shaft permitting sliding motion of the telescopic lens component in each of a first sliding direction and an opposite second sliding direction. The telescopic lens component includes a lens aperture that is positioned with respect to the phone receiving portion by displacement of the telescopic lens component in either the first or second sliding directions.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

FIGS. 1-7 depict an exemplary scope adapter 10 for coupling a mobile computing device such as a mobile phone to an endoscope. The adapter 10 enables portable recording and transmission of high definition video with audio commentary of any endoscopic examination undertaken using any type of mobile computing device or mobile phone having a camera. Optics provided with the adapter magnify the output from the endoscope to enable high resolution visualization of images. The adapter 10 is also designed to be light and portable.

Figure 1:
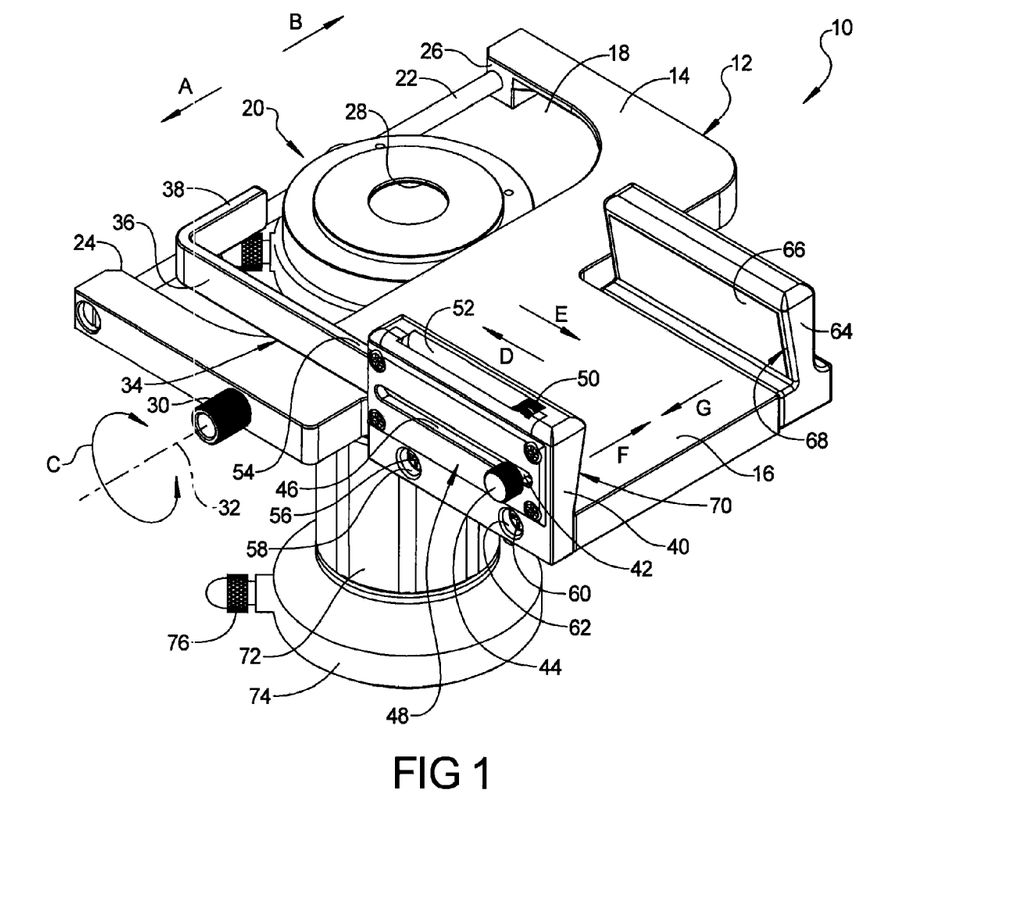
FIG. 1 is a top left perspective view of a scope adapter of the present disclosure.

Referring to FIG. 1, the adapter 10 includes a platform or U-shaped base 12 having a planar surface 14. The planar surface 14 extends onto a mobile computing device or phone receiving portion 16. An interior U-shaped cavity 18 is provided with U-shaped base 12 which receives a telescopic lens component 20. Cavity 18 permits sliding motion of the telescopic lens component 20 in each of a first sliding direction "A" and an opposite second sliding direction "B". A smooth exterior shaft 22 is coupled at opposite ends to each of a first base end 24 and a second base end 26 that define extents of cavity 18. Shaft 22 is non-rotationally fixed to first and second base ends 24, 26. The telescopic lens component 20 is slidably supported on the shaft 22 as will be better described in reference to FIG. 2. The telescopic lens component 20 includes a lens aperture 28 that is positioned with respect to phone receiving portion 16 by displacement of the telescopic lens component 20 in either the first or second sliding directions "A" or "B".

An adjustment nut 30 that can include a knurled exterior extends outwardly from one of the first or second base ends 24, 26 (in the exemplary aspect shown, the adjustment nut 30 extends from first base end 24). Adjustment nut 30 is axially rotatable with respect to a nut axis of rotation 32 in by manual rotation about an arc of rotation "C". During use, rotation of adjustment nut 30 incrementally displaces the telescopic lens component 20 in either of the first or second sliding directions "A" or "B" to provide fine adjustment of the position of lens aperture 28.

An L-shaped bar 34 includes a major length bar first portion 36 and a minor length bar second portion 38 which is shorter in length than bar first portion 36 and is oriented perpendicular to bar first portion 36. Bar first portion 36 is slidably received in a first clamp 40. The position of bar second portion 38 can be adjusted by moving either toward or away from first clamp 40, and is releasably fixed with respect to first clamp 40 using a releasable fastener 42 having a nut 44 on a free end thereof, which can also include a knurled surface. Fastener 42 engages the bar first portion 36 and can slide together with bar 34 in either a bar second portion 38 extending direction "D" or a retracting direction "E" by displacement within an elongated slot 46 created in first clamp 40. When a desired position of bar second portion 38 is reached, the nut 44 is manually tightened by axial rotation in a clockwise direction until nut 44 frictionally engages an outer wall 48 of first clamp 40, thereby releasably fixing the position of bar 34. Nut 44 can be released by rotation in a counterclockwise direction to allow repositioning bar 34. An alignment wheel 50 is rotatably captured in a second, upward opening slot 52 of first clamp 40. The alignment wheel 50 continuously contacts an upward facing surface 54 of bar first portion 36. Alignment wheel 50 provides for fine adjustment of the position of bar first portion 36. Bar first portion 36 can be moved to any desired extended or retracted position by manual rotation of alignment wheel 50.

A first biasing element retention fastener 56 is received in a first aperture 58 of first clamp 40 and extends through phone receiving portion 16. Similarly, a second biasing element retention fastener 60 is received in a second aperture 62 of first clamp 40 and extends through phone receiving portion 16. Each of the first and second biasing element retention fasteners 56, 60 threadably engage a second clamp 64 after passing through apertures (not shown) of phone receiving portion 16. The first and second clamps 40, 64 are oppositely displaceable with respect to each other and normally biased toward each other. A biasing element (not visible) such a coiled spring is disposed on first and second biasing element retention fasteners 56, 60. The first clamp 40 is fixedly retained by the element retention fasteners 56, 60 by a fastener force applied in a clamp direction "F", therefore first clamp 40 is fixed in position with respect to phone receiving portion 16. The biasing elements bias the second clamp 64 in a clamp direction "G" which is opposite to clamp direction "F", thereby allowing second clamp 64 to displace toward or away from first clamp 40, while being continuously biased in the clamp direction "F". A resilient material pad 66 is positioned on an inside facing surface 68 of second clamp 64 and also on an oppositely directed inside facing surface 70 of first clamp 40. The resilient material pads 66 help to frictionally retain a phone (shown and described in reference to FIG. 3) between the first and second clamps 40, 64.

Figure 4:
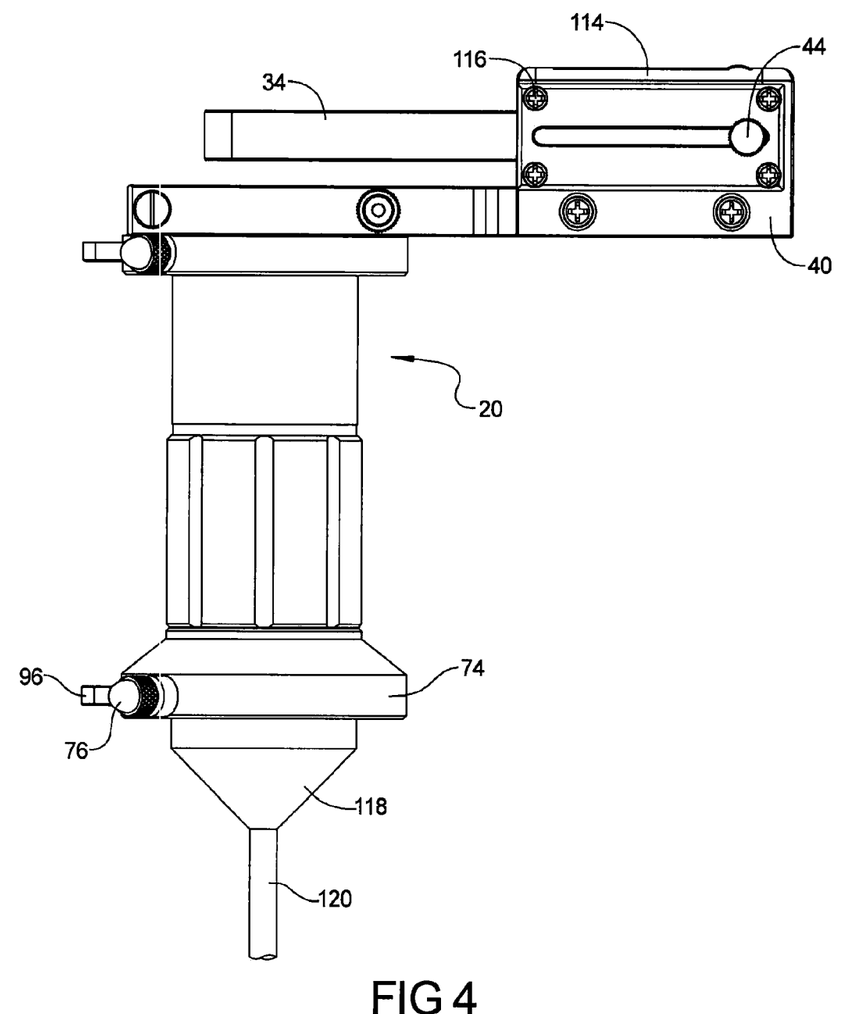
FIG. 4 is a left side elevation view of the scope adapter of FIG. 1.
Figure 5:
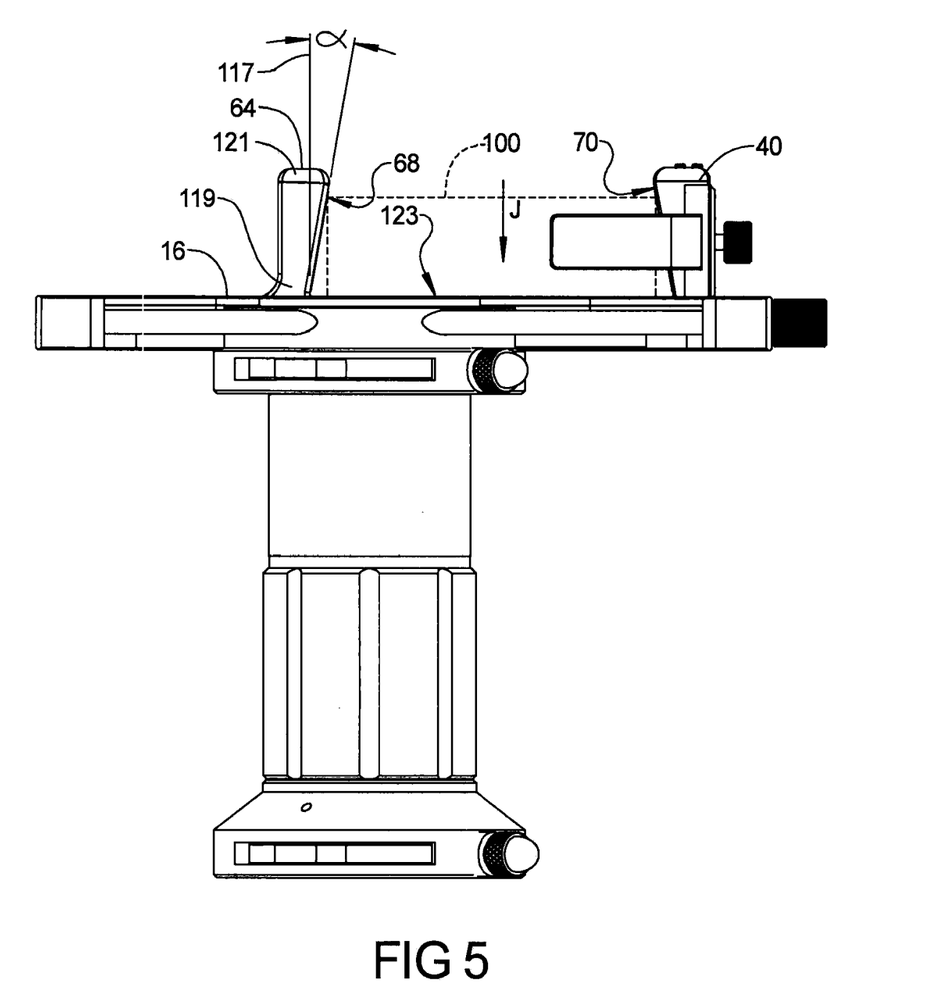
FIG. 5 is a front elevation view of the scope adapter of FIG. 1.
Figure 6:
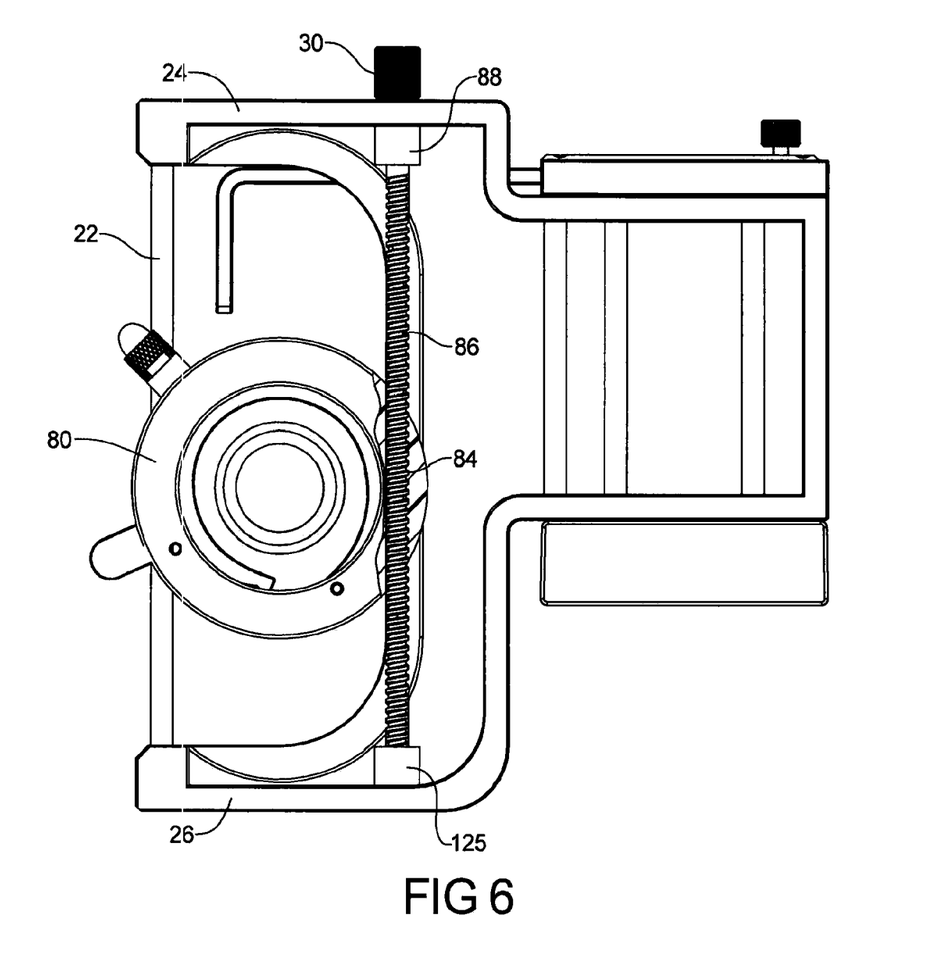
FIG. 6 is a bottom plan view of the scope adapter of FIG. 1.
Figure 7:
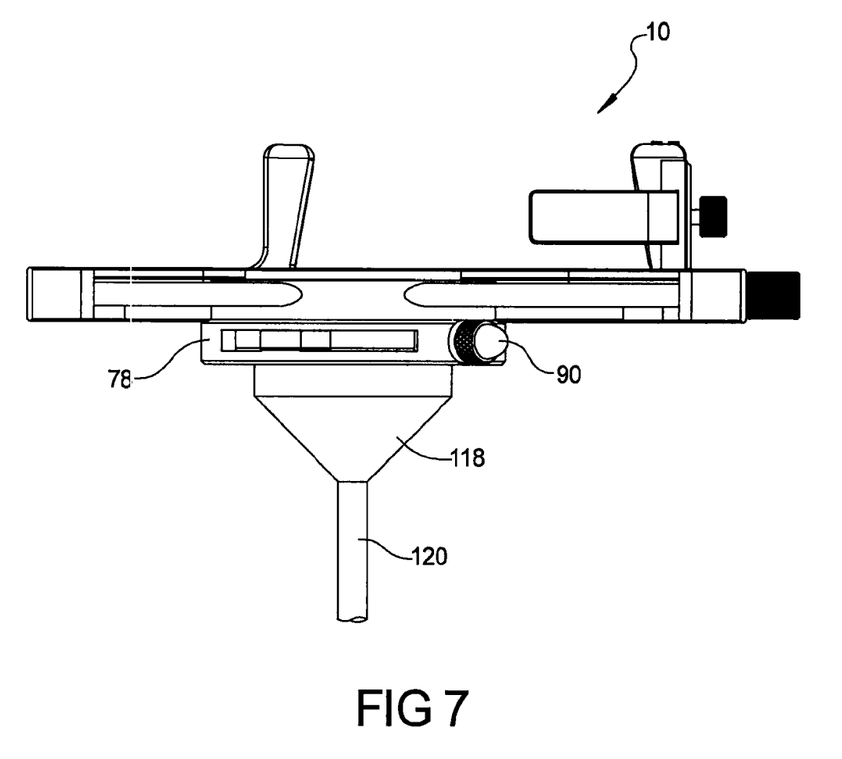
FIG. 7 is a front elevation view of the scope adapter of FIG. 1.

The telescopic lens component 20 includes a lens tube 72 which is oriented perpendicular to the planar surface 14, and an adapter 74 used to mate with an endoscope adapter (shown and described in reference to FIG. 4). A fixing nut 76 is provided to lock the endoscope onto the adapter 74.

Referring to FIG. 2 and again to FIG. 1, an adapter ring 78 of the telescopic lens component 20 is coupled to a positioning ring 80. The shaft 22 is slidably positioned within a smooth bore 82 of positioning ring 80, which closely matches a diameter of shaft 22. A threaded bore 84 is oppositely positioned in positioning ring 80 with respect to smooth bore 82, and is substantially parallel to smooth bore 82. The threaded bore 84 receives a threaded rod or threaded shaft 86 which is axially rotatable by manual rotation of adjustment nut 30. As the threaded shaft 86 is axially rotated, the positioning ring 80, and thereby the telescopic lens component 20 is incrementally displaced in either the first or second sliding directions "A" or "B". A first tube 88 integrally connected to the first base end 24 rotatably receives an un-threaded end of threaded shaft 86 such that threaded shaft 86 can axially rotate but is prevented from longitudinal displacement. A second tube (not visible in FIG. 3) integrally connected to second base end 26 rotatably receives a second un-threaded end of threaded shaft 86 and is shown and described in reference to FIG. 6.

Figure 2:
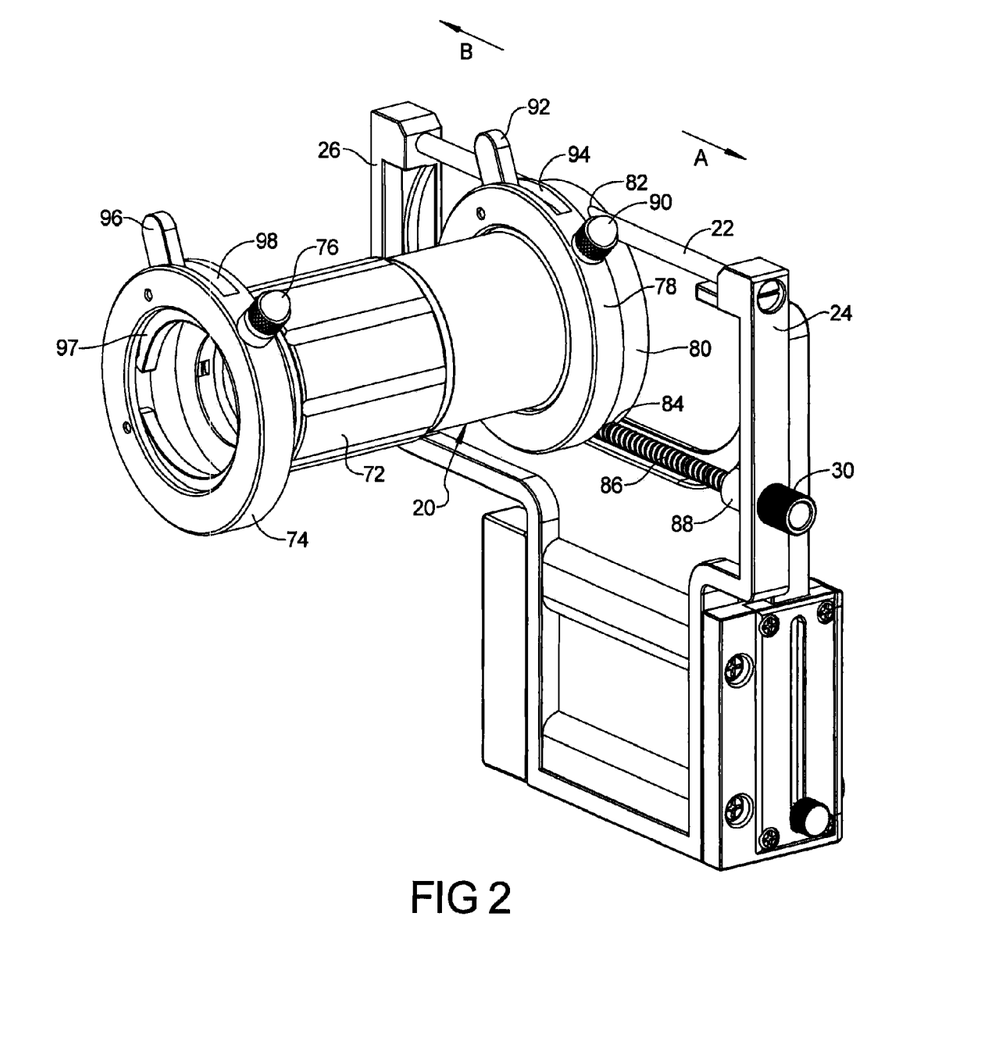
FIG. 2 is a bottom left perspective view of the scope adapter of FIG. 1.

The adapter ring 78 is provided with a fixing nut 90 which is similar to fixing nut 76, and is provided to lock the adapter ring 78 and thereby the telescopic lens component 20 onto positioning ring 80. A manually displaceable first lever 92 is disposed in an elongated slot 94 of adapter ring 94. The first lever 92 allows the telescopic lens component 20 to be connected to or released from engagement with positioning ring 80. A similar second lever 96 is provided in an elongated slot 98 of the adapter 74 which radially displaces an aperture ring 97 known in the art.

Referring to FIG. 3 and again to FIGS. 1-2, the adapter 10 is shown having a mobile computing device which according to several aspects is presented as a mobile phone 100 frictionally received between the first and second clamps 40, 64, the first and second clamps 40, 64 thereby defining first and second support contacts for the mobile computing device or phone 100. The phone 100 is moved in an installation direction "H" until a phone end wall 102 directly contacts an inner facing wall 104 of bar second portion 38, which thereafter releasably fixes phone 100. The position of bar second portion 38 is adjusted as previously discussed such that when phone 100 contacts bar second portion 38, a phone camera lens 106 has its focal centerline 108 co-axially aligned with the focal centerline of the lens aperture 28. Bar second portion 38 thereby provides a repeatable position for phone camera lens 106 with respect to lens aperture 28 and defines a third support contact for the phone 100, the first, second and third support contacts maintaining a repeatable position of the focal centerline 108 if the same phone 100 is removed and reconnected to adapter 10. It will be apparent that bar second portion 38 and the biased positioning of first and second clamps 40, 64 allow multiple different size phones to be used with adapter 10. As an additional aid to the sliding motion of telescopic lens component 20, a raised portion 105 of positioning ring 80 has an outer perimeter surface 107 that can slidably contact a wall 109 of the cavity 18 of U-shaped base 12 for the entire sliding motion of telescopic lens component 20.

Referring to FIG. 4, to assist in the assembly of bar 34 and nut 44 into first clamp 40, a releasable plate 114 is provided. Releasable plate 114 is fixed onto first clamp 40 using one or more fasteners 116. An endoscope adapter 118 is releasably engaged adapter 74 by first releasing a friction provided by nut 76 by rotation of nut 76 in a counterclockwise direction, followed by displacement of lever 96. The endoscope adapter 118 is then positioned in engagement with adapter 74, lever 96 is released, and nut 76 is again tightened. An endoscope 120 is then directed to a remote site desired for capturing a camera image defining a visual image of the remote site using phone 100.

Figure 3:
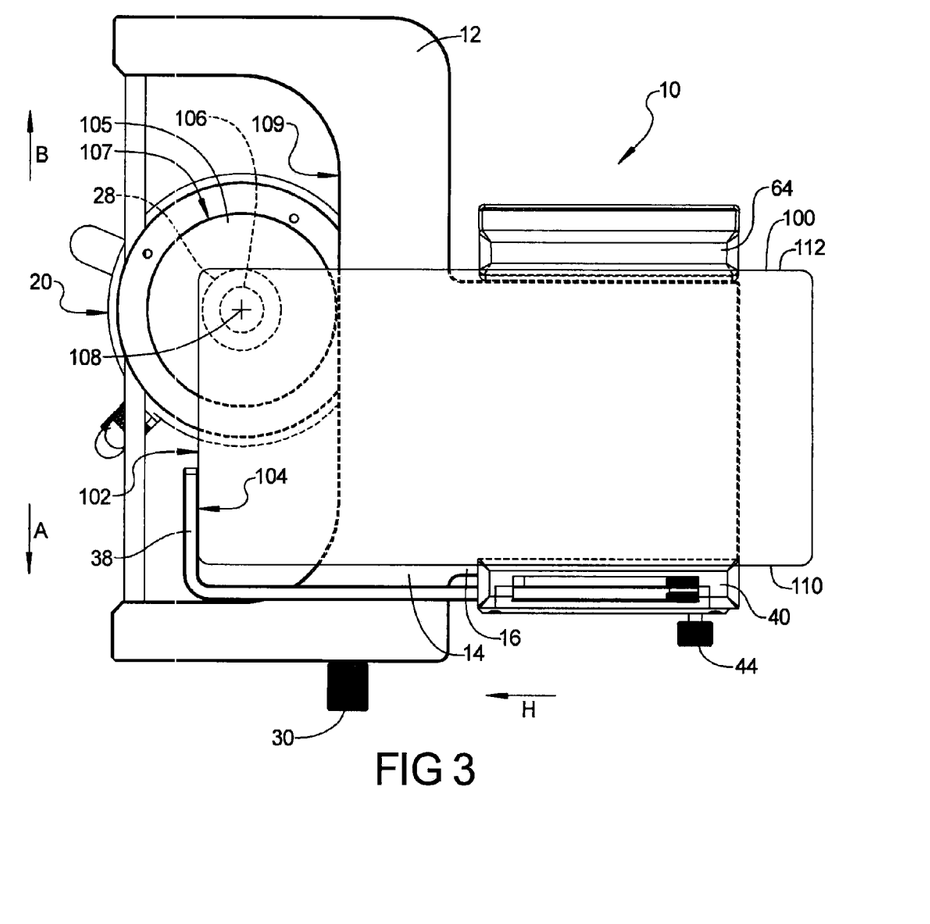
FIG. 3 is a top plan view of the scope adapter of FIG. 1.

Referring to FIG. 5 and again to FIGS. 1 and 3, it is anticipated a height of the phone 100 is shorter than a height of the first and second clamps 40, 64. In addition, the inside facing surfaces 68, 70 are each oppositely inwardly angled defining mirror image acute angles alpha (α) of approximately 15 to 20 degrees with respect to an axis 117 oriented perpendicular to phone receiving portion 16 between a lower end 119 and an upper end 121 of the first and second clamps 40, 64. Contact between the resilient material pad 66 provided on both of the inside facing surfaces 68, 70 and upper corners of phone 100 will therefore occur proximate to the upper ends 121 of the clamps, thereby producing a downward directed force "J" tending to hold phone 100 in contact with a planar surface 123 of the phone receiving portion 16.

Referring to FIG. 6 and again to FIGS. 1-2, in addition to being captured in the first tube 88, the threaded shaft 86 is further captured in a second tube 125 which is fixed to second base end 26. Similar to first tube 88, second tube 125 permits the free axial rotation of threaded shaft 86 when rotated using adjustment nut 30. The threaded bore 84 which is formed in positioning ring 80 engages the male threads of threaded shaft 86 to displace the positioning ring 80 and telescopic lens component 20 (not visible in this view), while the shaft 22 prevents axial rotation of telescopic lens component 20.

Referring to FIG. 7 and again to FIG. 4, the telescopic lens component 20 can be omitted from the assembly and the endoscope adapter 118 of the endoscope 120 can be directly engaged to the adapter ring 78. As previously described, the fixing nut 90 is released to allow installation of the endoscope adapter 118, and then manually tightened to lock the endoscope adapter 118 and endoscope 120 in position. In this aspect, the endoscope includes a lens aperture that is positioned with respect to the phone receiving portion 16 by displacement of the endoscope 120 in either the first or second sliding directions "A" or "B".

To use adapter 10, the phone 100 is inserted between the spring loaded clamps 40, 64 on the platform 12 and the phone end wall 102 is positioned in contact with the pre-adjusted position of bar second portion 38. The adjustment nut 30 is rotated which rotates threaded shaft 86 to displace the positioning ring 80 until the camera lens 106 of the phone 100 is positioned in alignment with the lens aperture 28. The telescopic lens component 20 is then locked in place using the adapter ring 78. The phone 100 is turned on and a camera application is opened to enable visualization through the telescopic lens component 20. The whole assembly of the telescopic lens component 20 can then be attached to any endoscope 120 using the endoscope adapter 118. This connection takes advantage of the standardized size and shape of known endoscopes. The adapter 74 includes the spring loaded lever 96 which is rotated with a finger and thumb to permit the advancement of the endoscope 120 into the adapter 74. Once released, the lever 96 locks the endoscope 120 in place so that it cannot exit without again rotating the lever 96. The adapter 74 positions the endoscope 120 in the central field of view of telescopic lens component 20 and thus, a magnified image from the endoscope 120 can be displayed on the cell phone 100.

Figure 8:
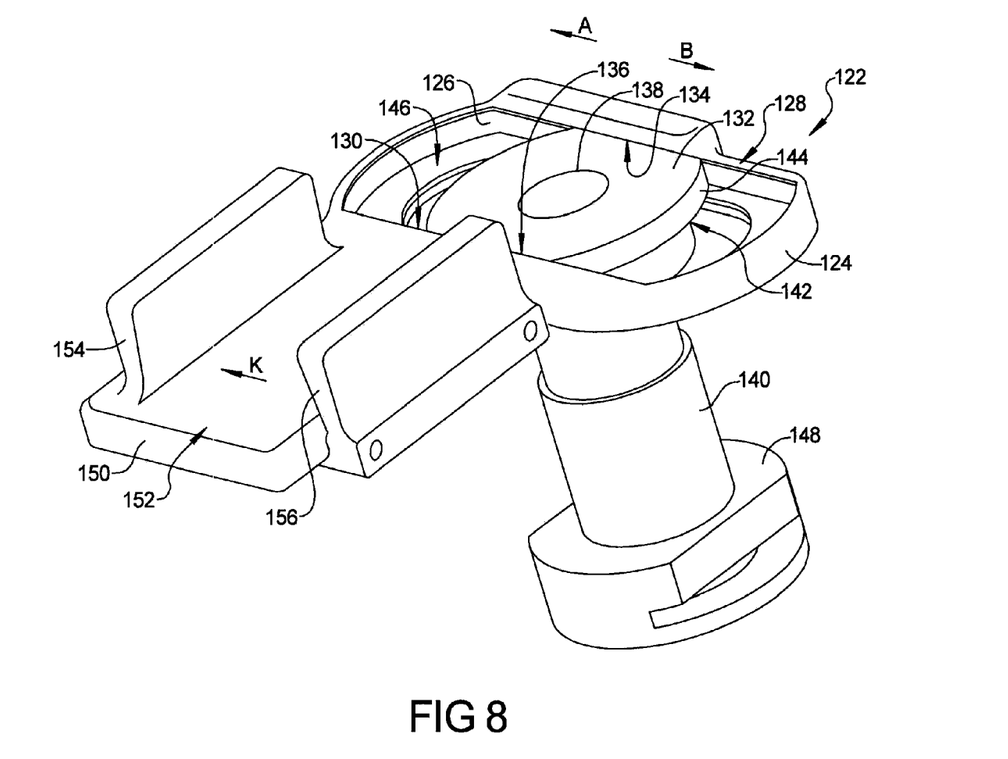
FIG. 8 is a top right perspective view of another embodiment of a scope adapter of the present disclosure.

Referring to FIG. 8, according to further aspects a scope adapter 122 is modified from scope adapter 10, therefore only the differences will be further discussed herein. Scope adapter 122 includes a platform or oval-shaped base 124 having an oval internal cavity 126. The oval internal cavity 126 includes opposed and parallel first and second walls 128, 130. A sliding member 132 is positioned in the oval internal cavity 126 and includes opposed first and second surfaces 134, 136 which individually slidably contact one of the first or second walls 128, 130 to control a position of a telescopic lens component 140 which is similar to telescopic lens component 20. A planar under-side surface 142 of a flange portion 144 of sliding member 132 directly contacts a planar upper facing surface of a wall 146 of base 124 within the internal cavity 126 to also guide sliding member 132. Cavity 126 permits sliding motion of the telescopic lens component 140 in each of the first sliding direction "A" and the opposite second sliding direction "B". An adapter 148 is provided at a free end of telescopic lens component 140 which functions similar to adapter 74 of scope adapter 10. The lens aperture 138 of telescopic lens component 140 is positioned with respect to a phone receiving portion 150 (which is similar to phone receiving portion 16) by displacement of the telescopic lens component 140 in either the first or second sliding directions "A" or "B".

The phone receiving portion 150 includes a planar surface 152 from which extends an integrally connected and therefore fixed first clamp 154. A second clamp 156 is releasably connected to phone receiving portion and is normally biased in a biasing direction "K" using springs similar to the method of biasing both first and second clamps 40, 64 of scope adapter 10. A first biasing element retention fastener 162 is received in a first aperture 164 of phone receiving portion 16. Similarly, a second biasing element retention fastener 166 is received in a second aperture 168 through phone receiving portion 150. Each of the first and second biasing element retention fasteners 162, 166 couple the second clamp 156 to phone receiving portion 150 when engaged with first and second apertures 164, 168 of phone receiving portion 16. The second clamp 156 is moveably displaceable with respect to first clamp 154 and is normally biased toward first clamp 154.

Figure 9:
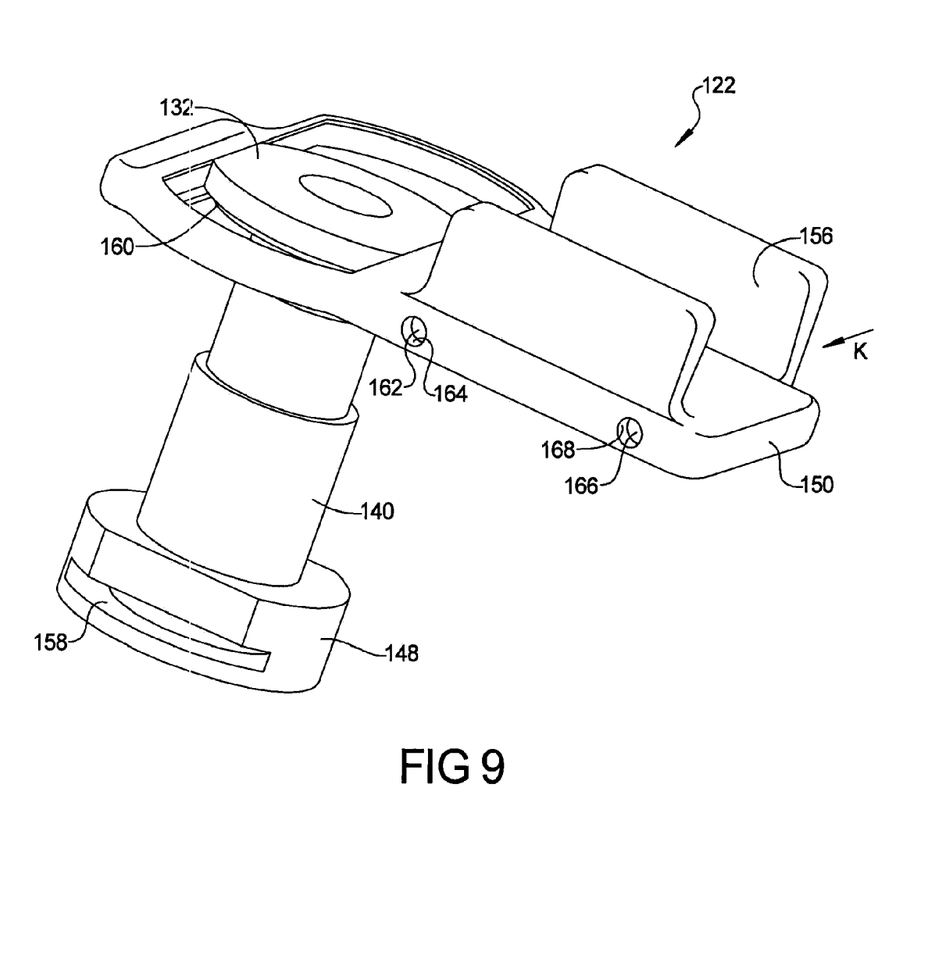
FIG. 9 is a top left perspective view of the scope adapter of FIG. 8.

Referring to FIG. 9, the adapter 148 includes an elongated slot 158 which receives a lever (not shown) similar in design and function to lever 96. A locking ring 160 is releasably coupled to the sliding member 132 which is tightened to lock a position of sliding member 132 within the internal cavity 126.

Figure 10:
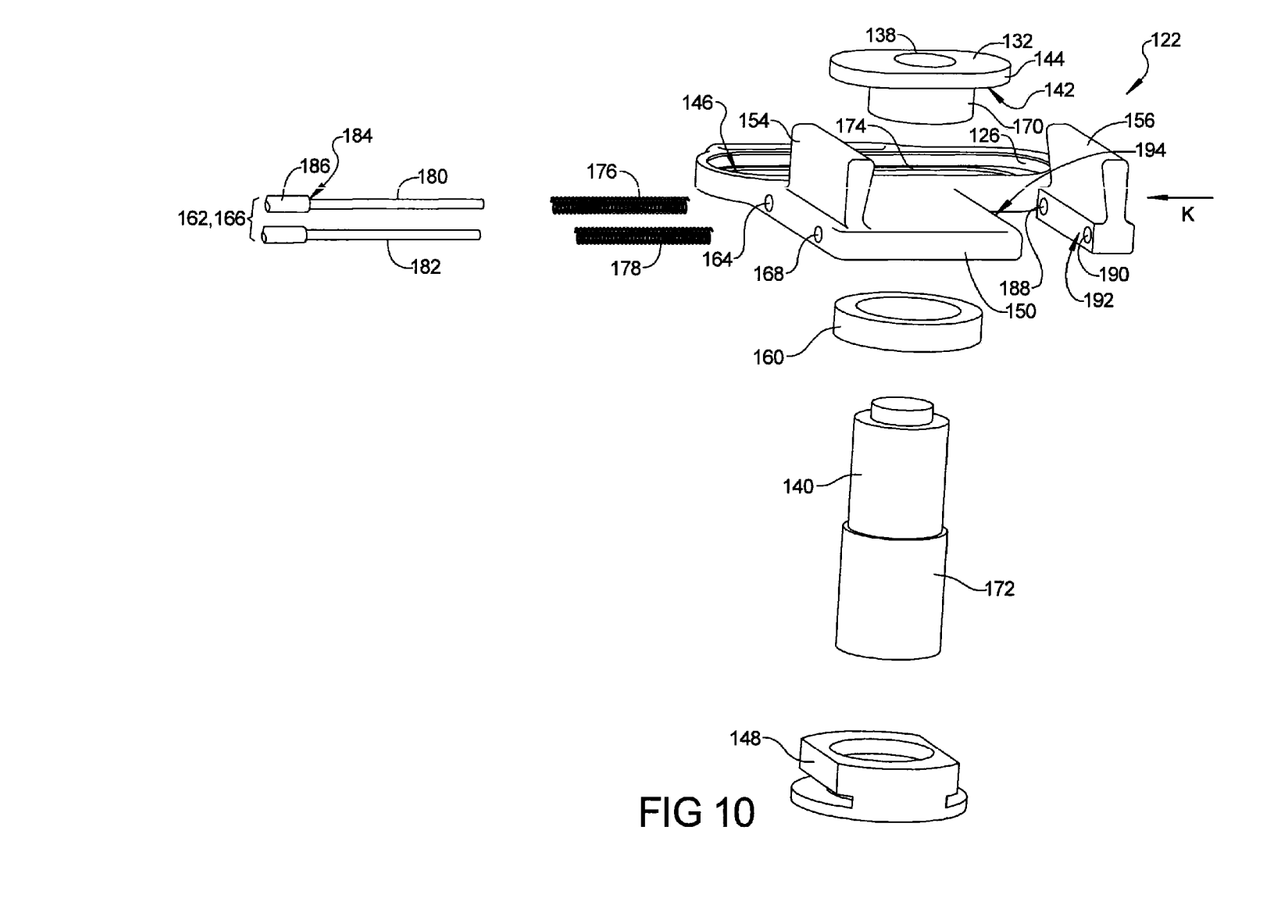
FIG. 10 is an exploded elevation view of the scope adapter of FIG. 8.

Referring to FIG. 10, the sliding member 132 includes a cylinder portion 170 that integrally extends from the planar under-side surface 142 of flange portion 144. The cylinder portion 170 is sized to be slidably received in an oval-shaped aperture 174 created in wall 146. The locking ring 160 contacts an underside surface of the wall 146 and engages the cylinder portion 170 to lock the sliding member 132 in a desired position within the internal cavity 126. The telescopic lens component 140 can include an axially extending and retracting portion 172 that moves either toward or away from the lens aperture 138 to change a focal length.

First and second biasing elements 176, 178 such as coiled springs are disposed onto the first and second biasing element retention fasteners 162, 166. The biasing elements 176, 178 are individually slidably received on a small diameter shank 180, 182 of either first or second biasing element retention fastener 162, 166. The biasing elements 176, 178 contact a shoulder 184 of a head 186 of each fastener, the head 186 having a larger diameter than the diameter of the shank. The biasing elements 176, 178 together with the first and second biasing element retention fasteners 162, 166 are inserted into the first and second apertures 164, 168 of phone receiving portion 150 and engage within first and second apertures 188, 190 of second clamp 156. The biasing elements 176, 178 pull a planar surface 192 of the second clamp 156 into direct contact with an oppositely facing planar side wall 194 of phone receiving portion 150. The biasing elements 176, 178 act when partially compressed to bias the second clamp 156 in the clamp biasing direction "K". It is also noted first and second biasing elements 176, 178, or similar biasing elements, can also be used on first and second biasing element retention fasteners 56, 60 of scope adapter 10.

Referring to FIGS. 8-10, to assemble adapter 122, the sliding member 132 is placed in a grooved portion or oval internal cavity 126 of the platform or base 124. The locking ring 160 is screwed onto an outer threaded portion of the sliding member 132 to lock it in place on the base 124. The endoscope connector assembly 140, 148 is screwed into the inner threaded lumen of the sliding member 132 to bring it flush with the planar surface 152 of base 124. In the exemplary embodiment, the endoscope connector assembly is comprised of the telescopic lens component 140 and the endoscope connector 148 which can be coupled or glued together.

The telescopic lens component 20, 140 is an important feature of the adapters 10, 122. Without it, the camera lens 106 of phone 100 cannot capture the details of the endoscopic visual image, meaning that if the phone 100 is placed up to the end of the endoscope 120 only a small dot would appear on the screen of the phone 100. Information from the endoscope 120 is present, but the image is too small to be viewed clearly, even using a digital zoom of the phone 100. Any telescopic lens that has an infinite focus is suitable for use with adapter 10. In the exemplary embodiment, the telescopic lens component 20, 140 is a three lens system with an internal image inverter and a variable focus ring. Such a telescopic lens component is commercially available from BMV Optical Technologies although other types of telescopic lenses are contemplated by this disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A scope adapter for coupling a mobile computing device to an endoscope, comprising:
    a platform base having a planar surface that extends onto a mobile computing device receiving portion that is capable of releasably receiving and stably supporting a mobile computing device,
    said platform base having a first base end and a second base end defining an interior cavity housing a positioning ring coupled to an adapter ring that is capable of coupling with a telescopic lens component or an endoscope adapter of the endoscope;
    a smooth exterior shaft connected at opposite ends thereof to each of the first and second base ends and spanning across the interior cavity, wherein a portion of said exterior shaft is further slidably positioned within a smooth bore in the positioning ring;
    a threaded shaft rotatably connected at opposite ends thereof to each of the first and second base ends and parallel to the smooth exterior shaft, wherein a portion of said threaded shaft is further rotatably positioned within and engaging a threaded bore in the positioning ring, such that when said threaded shaft is axially rotated the positioning ring and thereby the adapter ring is incrementally displaced for fine adjustment in either a first or second opposing direction parallel to and along the exterior shaft and threaded shaft to assist in placing a lens aperture associated with the positioning ring in alignment with a camera lens of the mobile computing device;
    the mobile computing device receiving portion including a first fixed clamp located proximate to and in a direction parallel to the first base end of the platform base, and a second spring-loaded displaceable clamp located proximate to and in a direction parallel to the second base end of the platform base and biased toward the first fixed clamp, such that the first fixed clamp and second spring-loaded displaceable clamp define first and second contact supports that are capable of releasably receiving and stably supporting the mobile computing device there between;
    the first fixed clamp further including an L-shaped bar having a major length bar first portion that is slidably received in the first fixed clamp and a minor length bar second portion oriented perpendicular to the bar first portion, wherein the position of the bar second portion can be adjusted by movement either toward or away from said first fixed clamp and secured using a releasable fastener, said bar second portion defining a third contact support to the mobile computing device which in concert with the first and second contact supports is capable of providing a repeatable position for alignment of the lens aperture with the camera lens.

2. The scope adapter for coupling a mobile computing device to an endoscope of claim 1, wherein the smooth exterior shaft is connected at opposite ends thereof to distal ends of each of the first and second base ends, and the threaded shaft is rotatably connected at opposite ends thereof to each of the first and second base ends proximate to the mobile computing device receiving portion.

3. The scope adapter for coupling a mobile computing device to an endoscope of claim 2, wherein the platform base is U-shaped and the interior cavity is U-shaped.

4. The scope adapter for coupling a mobile computing device to an endoscope of claim 1, further including an alignment wheel rotatably supported in an elongated slot of the first fixed clamp, the wheel continuously contacting an upper facing surface of the bar first portion, and wherein rotation of said wheel allows for fine adjustment of the bar first portion to adjust a position of the bar second portion with respect to the first fixed clamp.

5. The scope adapter for coupling a mobile computing device to an endoscope of claim 4, wherein a resilient material pad is positioned on an inside facing surface of the first fixed clamp and second spring-loaded displaceable clamp to assist in frictionally engaging the mobile computing device.

6. The scope adapter for coupling a mobile computing device to an endoscope of claim 5, wherein the first fixed clamp and second spring-loaded displaceable clamp have inside facing surfaces that are each oppositely inwardly angled defining mirror image acute angles, such that when a mobile computing device is placed between said first and second clamps there is produced a downward directed force that tends to hold the mobile computing device in contact with the planar surface of the mobile computing device receiving portion.

* * * * *